United States Patent [19]

Osborn

[11] Patent Number: 5,038,760

[45] Date of Patent: Aug. 13, 1991

[54] SURGICAL ORTHOPEDIC BACK SUPPORT GARMENT

[76] Inventor: Margaret R. Osborn, P.O. Box 264, Grinnell, Iowa 50112

[21] Appl. No.: 486,817

[22] Filed: Mar. 1, 1990

[51] Int. Cl.⁵ .............................................. A61F 5/02
[52] U.S. Cl. ......................................... 128/78; 2/44; 450/100; 450/109; 450/146
[58] Field of Search .................. 128/78, 99.1, 100.1, 128/102.1, 104.1, 105.1, 95.1, 96.1; 450/94, 100, 102, 104, 105, 134, 136, 140, 143, 146, 103; 2/44, 338

[56] References Cited

U.S. PATENT DOCUMENTS

| | | | |
|---|---|---|---|
| 2,104,699 | 1/1938 | O'Dell | 128/78 |
| 2,501,900 | 3/1950 | Herbener | 450/146 |
| 2,503,636 | 4/1950 | Rockwell | 450/103 |
| 2,587,307 | 2/1952 | Garduno | 450/100 |
| 3,013,561 | 12/1961 | Nelkin | 128/78 |
| 3,314,433 | 4/1967 | Champagne et al. | 128/520 |
| 3,396,730 | 8/1968 | Fox | 128/548 |
| 3,503,405 | 3/1970 | Porco | 450/102 |
| 3,717,143 | 2/1973 | Johnson | 128/78 |
| 4,143,663 | 3/1979 | Williams | 450/103 |
| 4,681,113 | 7/1987 | Coplans | 450/134 |
| 4,926,502 | 5/1990 | Miyamura | 450/146 |

*Primary Examiner*—Richard J. Apley
*Assistant Examiner*—Lynne A. Reichard

[57] ABSTRACT

A surgical orthopedic support garment designed for both utility and comfort by either sex includes front and back panels of non-elastic fabric material connected by flexible inserts to form a generally tubular configuration for ease in donning and removing and is provided with a fastenable crotch strap for securement after donning. Both panels are provided with permanent flexible stays to support the back and abdomen and the back panel is adapted to removably receive rigid stays for added support when needed. VELCRO tabs are attached to respective ends of the front panel and extend through keepers on corresponding ends of the back panel across the inserts for adjusting the tightness of fit without leaving loose or flapping ends and a zippered opening in the front panel provides flexibility in donning the garment. This garment is preferably made with no parts having a magnetic influence so as to avoid any possibility of intereference with a pacemaker or the like that might be in use by the wearer.

19 Claims, 2 Drawing Sheets

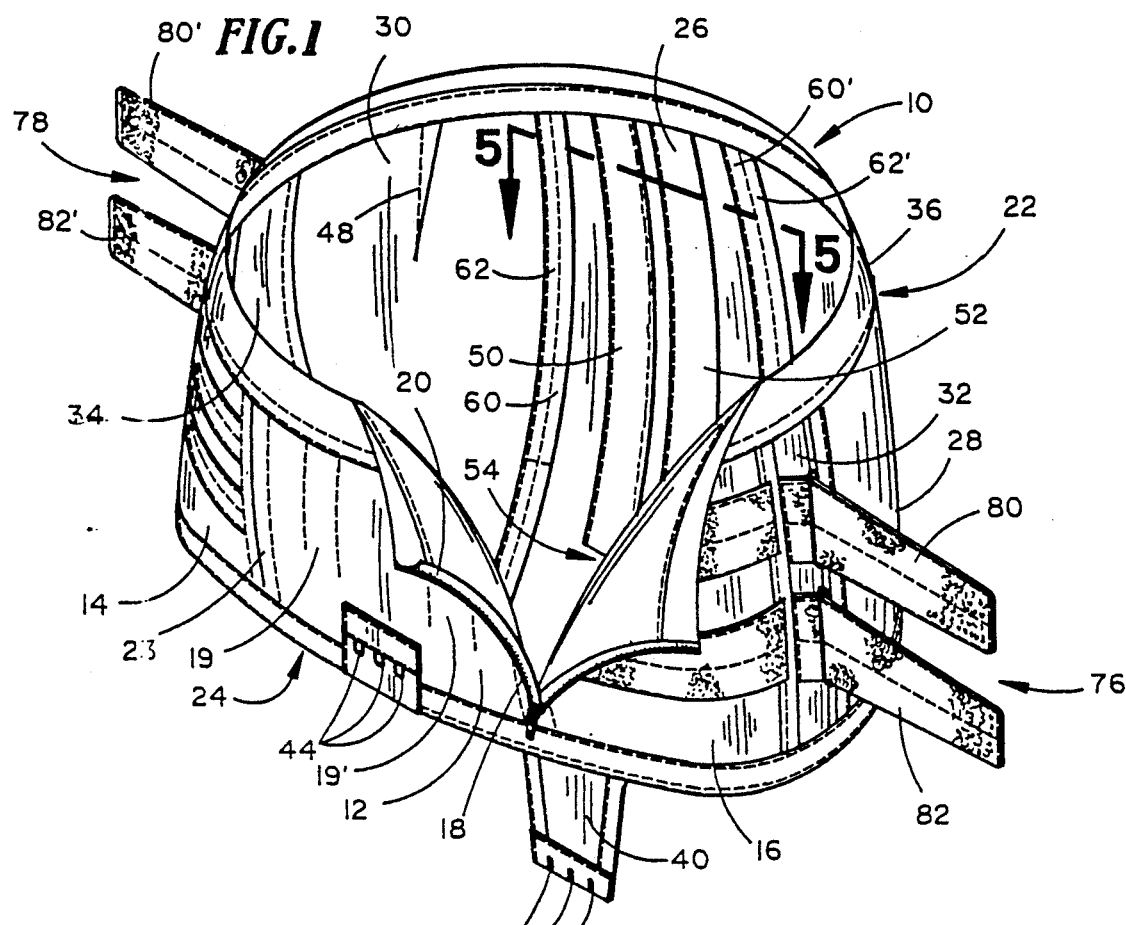

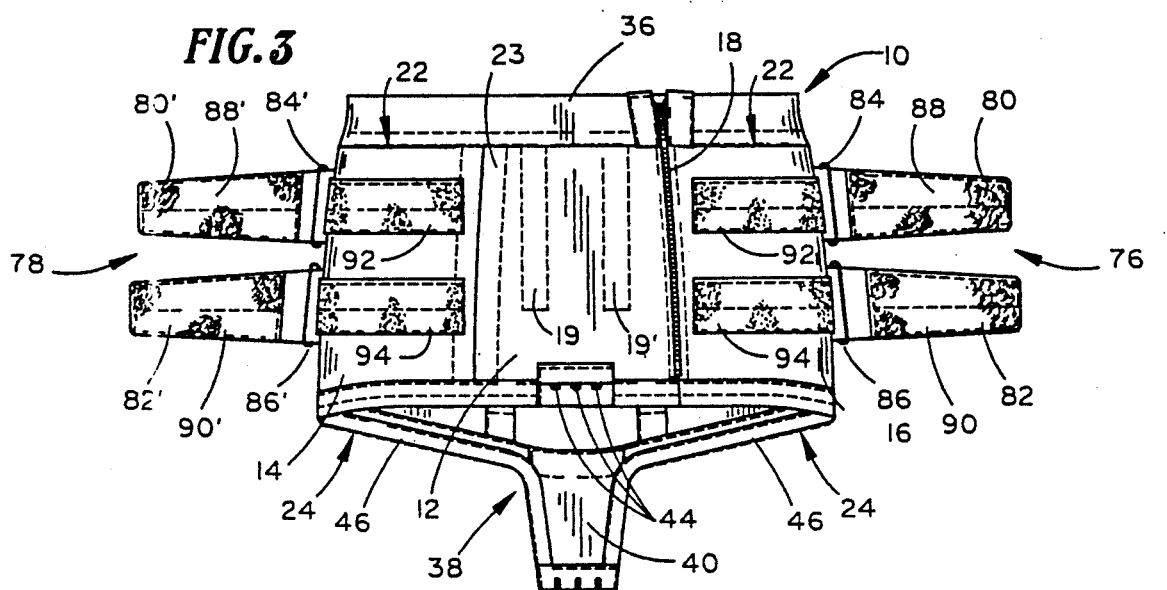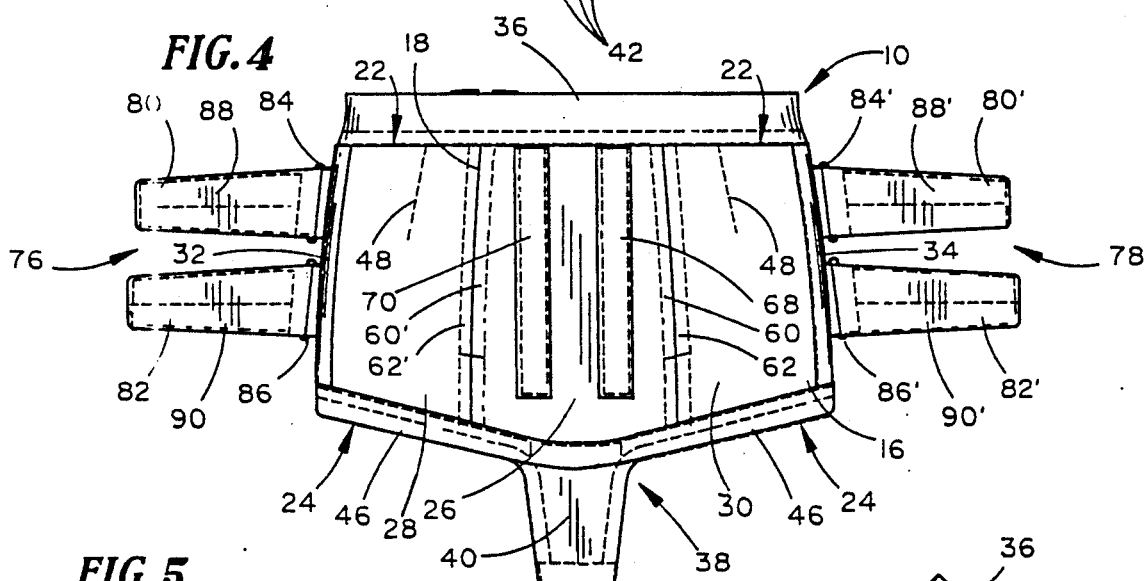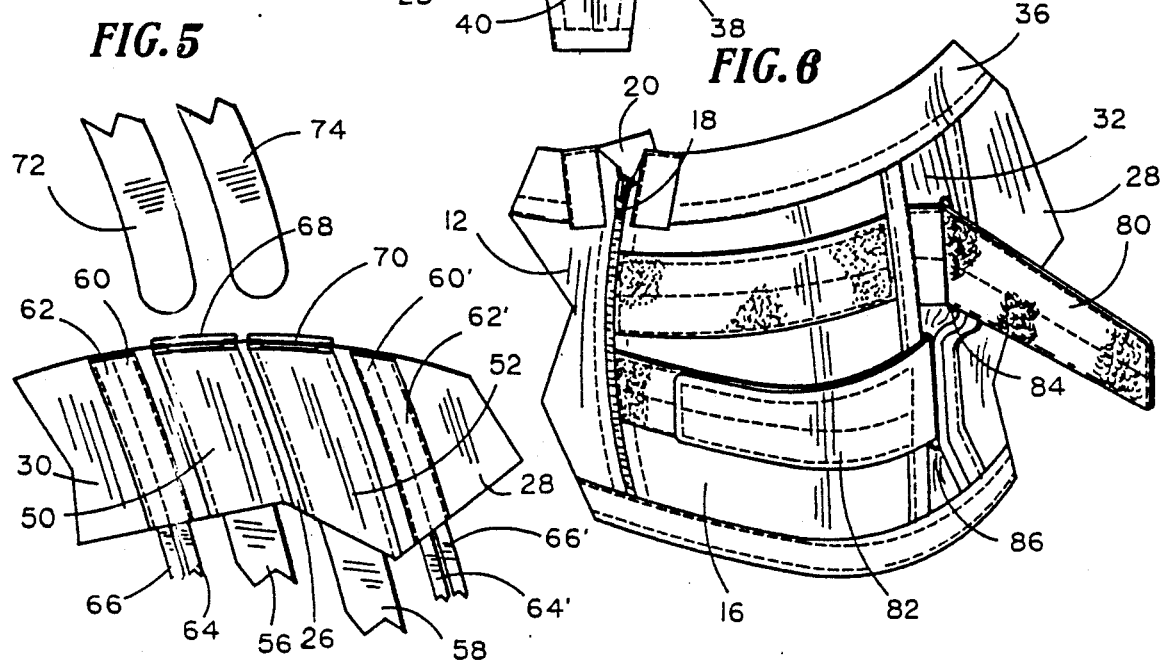

SURGICAL ORTHOPEDIC BACK SUPPORT GARMENT

BACKGROUND OF THE INVENTION

This invention relates to surgical orthopedic garments and more particularly to improvements in such garments designed to provide support for the relief of back problems and also abdominal support.

Back problems, for a variety of reasons, affect persons of all ages for which the use of some form of a support garment is a common expedient. One of the well known garments for this purpose is the wrap-around corset of a non-flexible material provided with a plurality of fixed stays, adjustment for fit by an arrangement of laces, straps and buckles and, generally, in garments for women, with garters for attachment to their hose. Notwithstanding the support provided by the corset form this type of garment has certain disadvantages in that there is no defined waistband or crotch so that even with the use of garters, the garment tends to ride up on the torso and the upper ends of the stays frequently become uncomfortable at the waist area.

Another type of garment in this class is exemplified by U.S. Pat. No. 3,396,730 in the form and style of a panty girdle with defined leg openings, a fixed crotch portion and fabricated from a plurality of elastic bands arranged in a variety of angular relationships to provide a tight fitting garment for the support intended. And in U.S. Pat. No. 3,314,433, there is disclosed a combination of a panty girdle and corset where there is a panty girdle type tubular body of elastic material having a crotch portion and defined leg openings together with front and back overlying panels of non-elastic material. This garment is provided with fixed encased stays as with a corset construction and also utilizes straps and buckles for tightening and adjustment. With such types of garments, it has been my observation that those with buckles and straps, where the ends often come loose from keeper loops, do not fit smoothly under outer wear and thus are unsuitable for wear with panty hose that most women use. Accordingly, it is one of the important objects of this invention to provide a surgical orthopedic support garment that overcomes such disadvantages noted and others as will appear.

It is another object herein to provide a support garment of the above class that is simple and easy to don and remove, is comfortable to wear and is highly efficient for its intended purpose.

More particularly, it is an object herein to provide a garment as characterized which is generally tubular in configuration for ease in donning and removing, has support elements in the back and abdominal areas, a fastenable strap for forming a crotch portion and leg openings after donning to keep the garment in a comfortable position and includes adjustment tabs that present no loose ends and require no buckles.

Still another object is to provide a garment of the class described that includes encased support stays in the back portion which is designed to removably receive additional stays to augment the support capability of the encased stays, if needed or desired.

A further object is to provide a garment as characterized that is preferably made with no parts having a magnetic influence so as to avoid any possibility of intereference with a pacemaker or the like that might be in use by a wearer.

SUMMARY

In accordance with this invention, a surgical orthopedic support garment designed for both utility and comfort by either sex includes front and back panels of non-elastic fabric material connected by flexible inserts to form a generally tubular configuration for ease of donning and removing and is provided with a fastenable crotch strap for securement after donning. Both panels are provided with permanent flexible stays to support the back and abdomen and the back panel is adapted to removably receive rigid stays for added support when needed. Velcro type tab fasteners attached to respective ends of the front panel extend through keepers on the back panel across the inserts for adjusting the tightness of fit with no loose or flapping ends and a zippered opening in the front panel provides flexibility in donning the garment. This garment is preferably made with no parts having a magnetic influence so as to avoid any possibility of interference with a pacemaker or the like that might be in use by the wearer.

The foregoing objects and such further objects as may appear herein, or be hereinafter pointed out, together with the advantages of this invention will be more fully discussed and developed in the more detailed description of the accompanying drawings.

BRIEF DESCRIPTION OF THE DRAWINGS

FIG. 1 is a perspective front view of a surgical orthopedic support garment embodying this invention shown in unfastened or open position ready for donning, FIG. 2 is a view similar to FIG. 1 but showing the garment fastened after it is donned with portions broken away to illustrate encased support components, FIG. 3 is an elevational front view of this garment showing the zipper on the front panel closed and the adjustment tabs and crotch strap in open position, FIG. 4 is an elevational rear view of the garment in FIG. 3, FIG. 5 is a fragmentary exploded perspective view taken on the line 5—5 of FIG. 1 to illustrate the removable auxiliary rigid stays for the back panel, and FIG. 6 is a fragmentary perspective view taken on the line 6—6 of FIG. 2 showing one adjustment tab open and one closed to illustrate the purpose of the insert between front and back panels for adjustment.

DESCRIPTION OF THE PREFERRED EMBODIMENTS.

Referring to the drawings, my new improved surgical orthopedic support garment is designated generally by the numeral 10 and is shown in FIG. 1 in open or unfastened position ready for donning and in FIG. 2 in closed or fastened position after it is donned.

Garment 10 is formed basically by a plurality of stitched together panels of non-resilient, non-stretchable corset material to have a generally tubular configuration defining a front and back portion and by this arrangement, there are no obstructing crotch or fixed leg openings for ease of donning and removal (FIG. 1) but is provided with such opening and crotch when worn (FIG. 2) as will later appear in more detail.

The front portion of garment 10 as best seen in FIG. 3 comprises a center panel 12 with the respective contigous right panel 14 and left panel 16 with panel 16 attached to panel 12 by a zipper fastener 18 as illustrated in FIG. 1 Zipper 18 is provided with an inner facing strip 20 (FIG. 1) to protect the body of the wearer from the zipper slide, and, as shown, zipper 18 is preferably between the center panel 12 and the left panel 16 since most users are righthanded and this location is thus more convenient for their use. However, it will be understood that zipper 18 may also be placed between panel 12 and the right panel 14, if desired, without affecting the utility of garment 10. Front panels 12, 14, 16 terminate at the top edge on a common plane 22 and similarly at the bottom edge on the common plane 24 that is substantially parallel to plane 22. On the inner side of the front center panel 12 in the central area are the elongated vertically spaced stitched cloth pockets 19, 19' extending from plane 22 to but spaced from plane 24 (FIG. 3) for encasing respective flexible relatively wide stays 21, 21' and at the side edge of panel 12 opposite to zipper 18 there is a narrower stitched pocket 23 for encasing a relatively narrow stay 25 for abdominal support. Stay 25 is preferably narrower than stays 21, 21' because it conforms better to the shape of the body in the area of support and is thus more comfortable in use.

The rear portion of garment 10 as best seen in FIG. 4 comprises a center panel 26 and respective contiguous left and right panels 28, 30. Rear left panel 28 is attached to the left front panel 16 by an insert strip of flexible material 32, lighter in weight than the other panels described, and a like insert 34 connects the right rear panel 30 to the right front panel 14. Inserts 32, 34 are of a flexible material such as batiste, and in their position intermediate the front and rear portions of garment 10 as described, they permit the garment to be selectively adjusted for tightness by forming into soft folds to reduce their widths as the front and rear portions of the garment are drawn together as will later appear in more detail. Panels 26, 28, 30 all terminate at the top at plane 22 previously described to form the tubular top edge of garment 10 to which there is preferably secured an elastic waistband 36 although a fitted waistband without elastic can also be used. While the bottom of the front of the garment 10 is generally planar as at 24, the bottom of the back is slightly lower than plane 24 by extending the rear center panel downwardly therefrom (FIG. 3) with rear panels 28, 30 tapered upwardly therefrom to plane 24 to form a crotch portion 38 provided with an extended crotch strap 40 that has one or more small hooks 42 for engaging complementary eyelets 44 attached to the bottom of the center front panel 12 and the entire bottom edge of garment 10, front and back, is preferably banded 46 in a well known manner. It will be understood that crotch portion 38 may be designed for comfortable use by either sex. The form shown is advantageous for female use either with or without a sanitary pad and particularly with panty hose since fastening means 42, 44 leave no exposed ends or sharp edges to snag any covering garment. It it also pointed out that the diameter of garment 10 at the waist area at plane 22 is slightly smaller than at plane 24 to better fit the body contour of the wearer and the rear panels 28, 30 are provided with suitable darts 48 to accommodate these different dimensions.

Stitched to the inside of the center rear panel 26 (FIGS. 1, 2) are two elongated parallel spaced vertical closed cloth pockets 50, 52 extending from the waistband 36 to a point 54 (FIG. 1) spaced slightly above the crotch portion 38 and positioned so that one will be at each side of the spine of the wearer for which support is provided by respective permanent relatively wide flexible stays 56, 58 of any suitable preferably material encased within said pockets. I have preferably made stays 56, 58 approximately 10½" long and ¾" wide but this not a requirement. Also, on the inner side intermediate panels 26, 30 and spaced parallel with pocket 50 are a pair of side by side similar but narrower pockets 60, 62 in each of which is permanently encased a respective narrow flexible stay 64, 66 similarly as with stays 56, 58. Spaced from pocket 52 intermediate panels 26, 28 is a similar arrangement of side by side narrow pockets and stays as described relative to pocket 50 and for which like parts are given like numerals primed. I have preferably made stays 64, 66, 64', 66' shorter than stays 56, 58 on the order of 9" long and approximately ¼" wide although this is not required and they are narrower than stays 56, 58 for the same reason described for stay 25.

To provide a means of selectively augumenting the central back area support stays 56, 58, I have stitched to the outer side of panel 26 in juxtaposition with pockets 50, 52, the respective corresponding outer pockets 68, 70, each open at the top near the waistband 36, and into which there can be removably inserted as desired or needed, the respective rigid stays 72, 74 of steel or other suitable material as illustrated in FIG. 5. By this arrangement, the support capability of garment 10 is not limited to manipulation of tightening or tensioning elements which is a limitation and disadvantage in similar garments.

Garment 10 is adjustably secured to the torso of the wearer by respective fastening assemblies 76 at the left side and 78 at the right side as seen in FIGS. 1, 3. Both assemblies 76, 78 are of like construction so only assembly 76 will be described in detail and like numbers primed for like parts will be given for assembly 78.

Assembly 76 comprises preferably a pair of elongated tapered tabs 80, 82 secured at corresponding ends by stitching to the left edge of front panel 16 which is also the front edge of insert 32 (FIG. 1) in parallel vertically spaced relationship between the upper and lower planes 22, 24 of garment 10 and opposite each stitched area of tabs 80, 82 is a respective elongated rigid loop or keeper 84, 86, that may be cloth covered, secured to the rear edge of insert 32 which is also the front edge of rear panel 28. Keepers 84, 86 and stays 72, 74 are preferably made from de-magnetized steel but any suitable material having no magnetic influence can be used so as to eliminate any possibility of interference with a pacemaker or the like that might be used by the wearer. The entire inner surfaces 88, 90 of tabs 80, 82 are covered by the rough side of a self adhering VELCRO type fastener and by this arrangement, the free ends of tabs 80, 82 are threaded through the respective keepers 84, 86 and then secured to soft elements of VELCRO type fastener strips 92, 94 stitched across the front panel 14 as best seen in FIG. 3. This, in effect, pulls the rear panel 28 towards the front panel 14 and the intermediate insert 32 will form into soft folds to reduce its width to provide the selective adjustment for comfort. This is illustrated in FIG. 6 where tab 80 is shown unfastened and tab 82 is shown fastened. Also, while I have preferably described a two tab component for assemblies 76, 78, it will be understood that this is also a matter of choice and only one tab or more than two may be used for the purposes indicated. My preference for two tabs is to permit individual adjustment at different areas of the torso, if desired.

It will be appreciated that the garment described is designed for ease and convenience in donning or removing, has features for keeping it in a comfortable position, is adaptable for use by either sex and for use with outer garments without protrusive bulging components and affords satisfactory support for the back.

Accordingly, in view of the foregoing, it is thought a full understanding of the construction and use of this new garment will be had and the advantages of the same will be appreciated.

I claim:

1. A surgical orthopedic support garment, comprising:
   a body member of generally tubular configuration formed of non-elastic fabric material adapted to encase the lower torso of the wearer,
   said body member comprising:
      respective opposed front and back portions with respective right and left opposed, spaced side edges and respective top and bottom edges, and
      a respective flexible fabric insert intermediate and connected to said back and front portions at said right and left side edges whereby the diameter of said body member can be selectively reduced by the movement of said side edges towards each other with the resulting folding of said inserts,
   fastenable tab means at each side edge of said body member operable relative to said front and back portions to selectively alter the diameter of the same,
   a zippered opening in said front portion communicating with the top edge thereof,
   a plurality of vertically disposed laterally spaced flexible stays secured to said front portion,
   a like arrangement of stays secured to said back portion,
   a crotch strap secured at one end to the central lower edge of said back portion and removable securable at its other end to the central bottom edge of said front portion,
   said zippered opening being at one side of said front portion, and
   said stays in said front portion comprising two of a like width in the central portion and one of a narrower width at the other side of said front portion.

2. A support garment as defined in claim 1, including:
   the bottom edge of said back portion being tapered downwardly and inwardly from said side edges to form a crotch portion, and
   said one end of said crotch strap secured to said crotch portion.

3. A support garment as defined in claim 1, including:
   a plurality of vertically disposed laterally spaced cloth pockets secured to the inner side of said front portion,
   a like arrangements of pockets secured to the inner side of said back portion, and
   a respective flexible stay encased within each of said pockets.

4. A support garment as defined in claim 1, including:
   said stays in said back portion comprising two of a like width disposed in the central portion and a pair of side by side stays of a lesser width at each respective side of said stays in the central portion.

5. A support garment as defined in claim 1 including means for removably attaching an auxiliary rigid stay to said back portion to augment the support afforded by said flexible stays.

6. A support garment as defined in claim 5 including the means for attaching an auxiliary rigid stay to said back portion being an elongated cloth open top pocket secured to the outer side of said back portion.

7. A support garment as defined in claim 6 including said cloth pocket being disposed in juxtaposition with one of said flexible stays in said back portion.

8. A support garment as defined in claim 1, including:
   a pair of vertically disposed elongated cloth open top pockets on the outer side of said back portion in lateral spaced relationship so that said pockets will be disposed at respective opposite sides of the spine of the wearer, and
   each of said pockets being in juxtaposition to a respective flexible stay in said back portion and adapted to removably receive a respective rigid stay to augment the support afforded by the stays in said back portion.

9. A support garment as defined in claim 1 in which said stays are of a material having no magnetic influence so as to not interfere with a pacemaker or the like that might be in use by the wearer.

10. A support garment as defined in claim 1 including said tab means being of self-adhering fabric fasteners free of any buckles and are always secured throughout their length to leave no loose ends or projections for comfortable use with and without an outer garment.

11. A surgical orthopedic support garment, comprising:
    a body member of generally tubular configuration of non-elastic fabric material adapted to encase the lower torso of the wearer,
    said body member defining front and back portions each with respective top and bottom edges,
    fastenable tab means at each side of said body member operable relative to said front and back portions to selectively tighten the same about the torso,
    a zippered opening in said front portion communicating with the top edge thereof,
    a plurality of vertically disposed laterally spaced cloth pockets on said front portion,
    a like arrangement of pockets on said back portion,
    a respective flexible stay encased in each of said pockets,
    the pockets on said back portion being on the inner side thereof,
    two of the pockets on said back portion being laterally spaced so they will be centrally disposed at respective opposite sides of the spine of the wearer,
    a respective open top cloth pocket attached to the outer side of said back portion in juxtaposition to said respective two pockets and adapted to removably receive a respective rigid stay to augment the support afforded by the stays in said back portion, and
    a crotch strap secured at one end to the central lower edge of said back portion and removably securable at its other end to the central bottom edge of said front portion.

12. A support garment as defined in claim 11, including:
    the bottom edge of said backportion being tapered downwardly and inwardly from said side edges to form a crotch portion, and
    said one end of said crotch strap secured to said crotch portion.

13. A support garment as defined in claim 11 in which said stays are of a material having no magnetic influence so as to not interfere with a pacemaker or the like that might be in use by the wearer.

14. A support garment as defined in claim 11 including said tab means being of self-adhering fabric fasteners free of any buckles and are always secured throughout their length to leave no loose ends or projections for comfortable use with and without an outer garment.

15. A support garment as defined in claim 11 wherein the pockets with encased stays on the inner side of said back portion include a respective pair of side by side pockets with encased stays spaced at each side of said centrally disposed pockets and of lesser width thereof.

16. A surgical orthopedic support garment, comprising:
    a body member of generally tubular configuration formed of non-elastic fabric material adapted to encase the lower torso of the wearer,
    said body member comprising: respective opposed front and back portions with respective right and left opposed, spaced side edges and respective top and bottom edges, and
    a respective flexible fabric insert intermediate and connected to said back and front portions at said right and left side edges whereby the diameter of said body member can be selectively reduced by the movement of said side edges towards each other with the resulting folding of said inserts,
    fastenable tab means at each side edge of said body member operable relative to said front and back portions to selectively alter the diameter of the same,
    a zippered opening in said front portion communicating with the top edge thereof,
    a plurality of vertically disposed laterally spaced flexible stays secured to said front portion,
    a like arrangement of stays secured to said back portion,
    a crotch strap secured at one end to the central lower edge of said back portion and removably securable at its other end to the central bottom edge of said front portion, and
    means for removably attaching an auxiliary rigid stay to said back portion to augment the support afforded by said flexible stays.

17. A support garment as defined in claim 16 including the means for attaching an auxiliary rigid stay to said back portion being an elongated cloth open top pocket secured to the outer side of said back portion.

18. A support garment as defined in claim 17 including said cloth pocket being disposed in juxtaposition with one of said flexible stays in said back portion.

19. A surgical orthopedic support garment, comprising:
    a body member of generally tubular configuration formed of non-elastic fabric material adapted to encase the lower torso of the wearer,
    said body member comprising:
    respective opposed front and back portions with respective right and left opposed, spaced side edges and respective top and bottom edges, and
    a respective flexible fabric insert intermediate and connected to said back and front portions at said right and left side edges whereby the diameter of said body member can be selectively reduced by the movement of said side edges towards each other with the resulting folding of said inserts,
    fastenable tab means at each side edge of said body member operable relative to said front and back portions to selectively alter the diameter of the same,
    a zippered opening in said front portion communicating with the top edge thereof,
    a plurality of vertically disposed laterally spaced flexible stays secured to said front portion,
    a like arrangement of stays secured to said back portion,
    a pair of vertically disposed elongated cloth open top pockets on the outer side of said back portion in lateral spaced relationship so that said pockets will be disposed at respective opposite sides of the spine of the wearer,
    each of said pockets being in juxtaposition to a respective flexible stay in said back portion and adapted to removably receive a respective rigid stay to augment the support afforded by the stays in said back portion, and
    a crotch strap secured at one end to the central lower edge of said back portion and removably securable at its other end to the central bottom edge of said front portion.

* * * * *